United States Patent [19]
Bundy et al.

[11] Patent Number: 5,767,385
[45] Date of Patent: Jun. 16, 1998

[54] AUTOMATED FORCED-CHOICE DYNAMIC-DILUTION OLFACTOMETER AND METHOD OF OPERATING THE SAME

[75] Inventors: Dwaine S. Bundy, Ames, Iowa; Wen-Hua Huang, Vancouver, Canada; Steven J. Hoff, Jewell, Iowa; Qianbao Liu, Mayaguez, Puerto Rico; Xiwei Li, Ames, Iowa

[73] Assignee: Iowa State University Research Foundation, Inc., Ames, Iowa

[21] Appl. No.: 794,873

[22] Filed: Feb. 5, 1997

[51] Int. Cl.[6] ............................................. G01N 1/26
[52] U.S. Cl. ............................................. 73/23.34
[58] Field of Search ................................... 73/23.34

[56] References Cited

U.S. PATENT DOCUMENTS

| | | | |
|---|---|---|---|
| 3,882,713 | 5/1975 | Nishida et al. | 73/23.34 |
| 3,902,851 | 9/1975 | Dravnieks | 73/23.34 |
| 4,411,156 | 10/1983 | Lowe | 73/23.34 |
| 5,177,994 | 1/1993 | Moriizumi et al. | 73/23.34 |

FOREIGN PATENT DOCUMENTS

| | | | |
|---|---|---|---|
| 4-4186139 | 7/1992 | Japan | 73/23.34 |

Primary Examiner—Ronald L. Biegel
Attorney, Agent, or Firm—Zarley, McKee, Thomte, Voorhees & Sease

[57] ABSTRACT

An automated forced-choice dynamic-dilution olfactometer has an odor evaluation module having two or more panelist stations, with a plurality of sniffing ports at each station. At least one signal element at each station is connected to a data control unit. Separate air lines are connected to one each of the sniffing ports at each station. One of the air lines has an odor introduction port. The method of detecting an odorous stream of air in an automated forced-choice dynamic-dilution olfactometer and method of operating the same olfactor system comprises the steps of providing an odor evaluation module having at least two panelist stations; providing a plurality of sniffing ports at each station; providing a data control unit and connecting the control unit to a signal element at each station, providing separate air lines to one each of the sniffing ports at each station so that individual panelists at each station can separately sniff the air in each line, introducing an odor into one of the air lines, having the panelists at each station sniff each sniffing port to determine which air line contains the odor, and having each panelist actuate the signal element to advise the data control system as to which air line contains the odor.

13 Claims, 4 Drawing Sheets

AUTOMATED FORCED-CHOICE DYNAMIC-DILUTION OLFACTOMETER AND METHOD OF OPERATING THE SAME

This invention was made with government support under the United States Department of Agriculture using Hatch funds; IAHEES project numbers IA 3013 and IA 3140. The government has certain rights to this invention.

This application is based upon the applicants' provisional application Ser. No. 60/011,215 filed Feb. 6, 1996.

BACKGROUND OF THE INVENTION

The livestock industry in the United States is expanding rapidly. However, expansion is being restricted by environmental problems. Odor is one of the major environmental problems for the livestock industry. The odors produced by livestock units originate from manure, ventilation exhaust air from farm buildings, animals, and feed.

Before progress can be made on the abatement of this odor nuisance, a reliable method is required for quantifying odor concentration. Olfactometric measurements are of prime importance in the study and evaluation of the odor problem. The concentration of odor in air is measured with an olfactometer. The olfactometer is being used in research aimed at reducing odor problems associated with the livestock industry.

A variety of olfactometry techniques have been used to measure odor concentration. They include the syringe dilution method, the scentometer, the butanol olfactometer, and various dynamic olfactometers. Many of these devices do not produce reliable results and this has limited the effectiveness of past odor research and regulation. In most research and regulatory institutions in Europe and Australia, dynamic-dilution olfactometry is now accepted as the 'de facto' standard. Research on current dynamic dilution olfactometers started in the United States in the 1970's which led to the American Society of Testing Material (ASTM) standard E679, "Determination of odor and taste by a forced-choice ascending concentration series methods of limits" (ASTM, 1979).

This invention is directed to an automatic forced-choice, dynamic-dilution olfactometer aimed at measuring odor concentration associated with air from and surrounding livestock buildings.

Odor is the sensation caused by odorant acting on the sense of smell. Odor concentration measurement is basically a threshold measurement. It measures quantitatively how many times more concentrated the odor is than its threshold concentration. The measurement is made through an olfactometer and panelists. A variety of olfactometry techniques have been used to measure odor concentration.

Dynamic Olfactometry

Odor concentration is measured in terms of an odor unit (ou), or how many times more concentrated the sample is than the threshold concentration. Olfactometry is the use of the human nose as the sensor for odor. Dynamic olfactometry is the technique whereby a stream of odorous air is continuously diluted with a stream of odor-free air before being presented to a panel of people through a sniffing port. Odor concentration is determined by finding the odor detection threshold. This is defined as the dilution of the original odor sample at which half the panel can just detect the odor while the other half cannot detect the odor. Detection of the odor is the sole criterion and not recognition or assessment of the strength, character, or quality of the odor. The threshold is usually ½ to ¹⁄₁₀ the recognition or quality threshold.

The detection threshold is found by presenting the panel with a series of dilutions of the odor sample. These dilutions should cover the range from where none of the panelists can detect the odor to where all panelists can detect the odor. This procedure allows determination of the perception curve, or the relationship between dilution and the percentage of the panel which correctly detects the odor.

TABLE 1

Properties of dynamic olfactometry

| Item | Setting |
|---|---|
| Method used | forced-choice |
| Number of dilution steps | 5(minimum) |
| Order of dilution steps | increasing concentration |
| Factor between dilutions | 2 < factor < 3 |
| Panel number | provisionally 8 |
| Dilution range | up to 25000 |
| Shape of sniffing ports | conical with diameter 4–7 cm maximum angle 7° |

As determined by olfactometry, concentration is a dimensionless quantity equal to the dilution factor that must be applied to the sample to reach the odor detection threshold. For example, if a sample is diluted by a factor of 100 before the threshold is reached, it will have an odor concentration of 100 DT.

SUMMARY OF THE INVENTION

The device of this invention will include the following:

Four response buttons per panelist from which each panelist indicates the port believed to contain the odor;

A signal light which tells each panelist to begin sniffing and to indicate the conclusion of each test;

Data latches for each button that serve to store each panelist's response;

A multiplexing system that allows the data latches for each panelist to be read in sequence through a computer link;

A program used to analyze and process the data;

An input/output analog signal board for the input analog signal from the pressure transducer and flow meter and for sending out analog signals to each instrument;

A digital output signal board with relays for controlling the automatic valves;

A personal computer linked to the DAAC system.

The method of this invention comprises the following:

Step 1. Operator secures an odorous sample and starts the olfactometer control system. The start-up control panel appears on the monitor.

Step 2. The operator activates the START button and is instructed to enter the sample name.

Step 3. After the sample name is entered, the operator is instructed to select the starting dilution level.

Step 4. The operator selects a number from 1 to 12 corresponding to the desired dilution level from $1:2^3$ to $1:2^{14}$, respectively. The control system begins establishing the desired dilution level and responds with "System increasing pressure, please wait". The pressure signal display in the "Sample Pressure Box" changes dynamically until the pressure reaches 3.5 PSI; the program responds with "Dilution is level A please begin sniffing".

Step 5. The four panelists begin sniffing their respective 3 ports and depress the button corresponding to the sniffing port which they perceive contains the odor. The response of the four panelists is displayed in the monitor by changing signal lights on the computer screen. There were 8 signal lights (4 for the evaluation buttons and 4 for the accept buttons) located on the monitor.

Step 6. If all four panelists select the correct port corresponding to the odorous sample, then the statement "Evaluation Successful" appears and the test concludes.

DESCRIPTION OF THE PREFERRED EMBODIMENT

The principle of odor measurement is that all materials which come in contact with the odor must be of low absorption; suitable materials being glass, Teflon®, and stainless steel pipes and fittings as were used in the olfactometer system.

Figure 1:
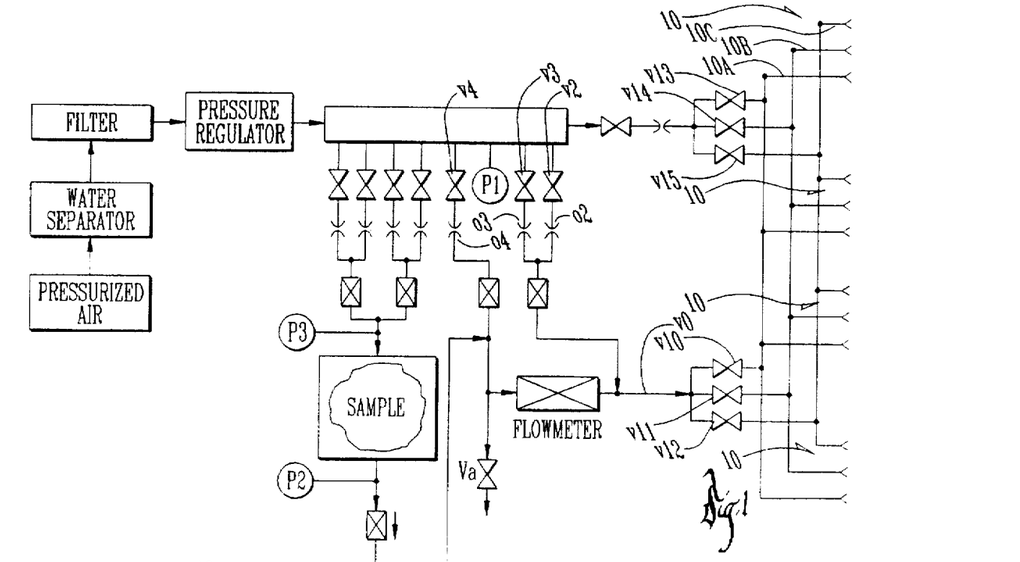
FIG. 1 is an automated forced-choice dynamic-dilution olfactometer and method of operating the same.

FIG. 1 is a schematic diagram of the dilution system. This system dilutes the odor sample to the required range, provides each panelist with three air streams (one odorous and two odor free) of the same airflow rate, and randomly switches the port containing the diluted odorous airflow. It also allows determination of the detection threshold for standard odorants.

The odor free air is supplied by compressed air regulated to 32 PSI. The compressed air passes through an activated charcoal filter to remove particulates, oil and to remove water vapor before entering the dilution system. The total airflow descantant rate through the olfactometer is about 250 1/min, as described below.

A combination of four on/off automatic valves (v5–v8) with four orifices o5 (d=0.026 inch), o6 (d=0.024 inch), o7 (d=0236 inch) and o8 (d=0.0126 inch) allow odor-free air to enter the sample container forcing the sample air into the dilution system by positive displacement.

The pneumatic dilution system also uses two on/off automatic valves v2 and v3 along with two orifice plates o2 (d=0.0635 inch) and o3 (d=0.070 inch) and an electronic proportioning control valve (Va) to dilute the sample with fresh-air to various rates depending on the dilution level desired. Details related to each dilution level are shown in Table 2. An on/off automatic valve v4 with orifice plate o4 (d=0.070 inch) is used to predilute the sample so that the maximum dilution level of 1:16384 can be attained.

TABLE 2

The calculation of dilution level

| Level | $O_3$ | $Q_3$ (l/min) | $Q_{pa,o4}$ | $Q_{pa,f}$(l/min) | $O_d$ | $Q_d$(l/min) | dilution ratio |
|---|---|---|---|---|---|---|---|
| 1 | $O_6$ | 8 | X | 8 | $O_2$ | 56 | $2^3$ |
| 2 | $O_7$ | 7.7 | X | 4.1 | $O_3$ | 62 | $2^4$ |
| 3 | $O_8$ | 3.6 | X | 2 | $O_3$ | 62 | $2^5$ |
| 4 | $O_6$ | 8 | 62 | 9.8 | $O_3$ | 62 | $2^6$ |
| 5 | $O_8$ | 3.6 | 62 | 9.29 | $O_2$ | 56 | $2^7$ |
| 6 | $O_8$ | 3.6 | 62 | 4.6 | $O_3$ | 62 | $2^8$ |
| 7 | $O_8$ | 3.6 | 62 | 3.3 | $O_3$ | 62 | $2^9$ |
| 8 | $O_8$ | 3.6 | 62 | 1.12 | $O_3$ | 62 | $2^{10}$ |
| 9 | $O_8$ | 3.6 | 62 | 0.55 | $O_3$ | 62 | $2^{11}$ |
| 10 | $O_8$ | 3.6 | 62 | 0.277 | $O_3$ | 62 | $2^{12}$ |
| 11 | $O_8$ | 3.6 | 62 | 0.138 | $O_3$ | 62 | $2^{13}$ |
| 12 | $O_8$ | 3.6 | 62 | 0.069 | $O_3$ | 62 | $2^{14}$ |

After the sample air and the odor free air pass through their respective paths they are mixed together to give the required dilution. A dilution of up to 1:16348 times can be obtained. Thus, concentrations of the odor can be delivered to the panelists in the range between $1:2^3$ and $1:2^{14}$. The mixed air stream Vo was further divided into four streams; one for each panelist station 10 (see FIG. 1).

Figures 2, 2A:
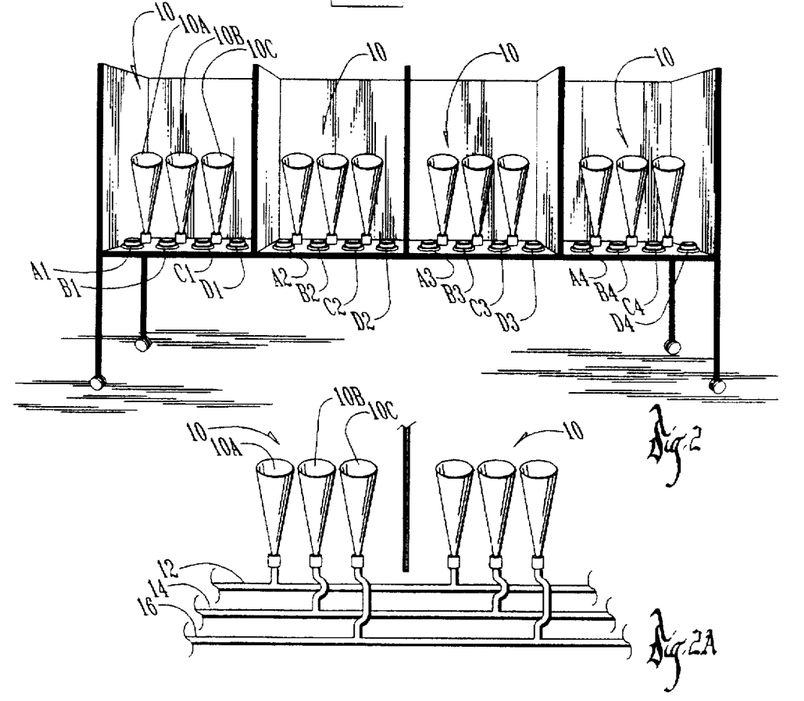
FIG. 2 is a perspective view of the panel response system (i.e. odor evaluation module)
FIG. 2A is a partial schematic view of the air lines connecting the sniffing ports.
Figure 5:
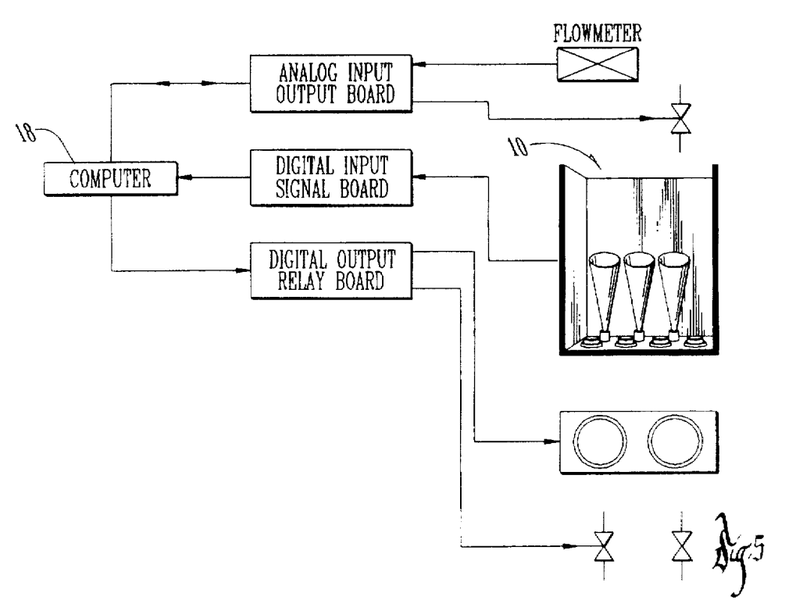
FIG. 5 is a schematic diagram of the data acquisition, data analysis, and automatic control system (DAAC)

FIG. 2 is a schematic diagram of the panel response system. In the forced choice olfactometer of this invention, each panelist tests the air from more than one, and preferably three, sniffing ports 10A, 10B and 10C. Each station 10 has four response buttons (A1, B1, C1, D1–A4, B4, C4, D4) operatively connected to computer 18 (FIG. 5). The A, B and C series buttons pertain to sniffing ports 10A, B and C, respectively. The D series buttons are the "accept" buttons. The panel response system of this invention uses six on/off automatic valves (v10–v15) (see FIG. 3) that allow the dilution system to switch the diluted odorous air stream randomly between the three lines, 12, 14 and 16 (FIG. 2A) (one odorous; two odor free) so that panelists have no knowledge of which port will contain the odor. The panelist has to decide which contains the odorous air. At concentrations near the threshold, the panelist will select the port that he or she believes is most likely to contain the odor.

The main criterion of the sniffing ports (10A, 10B and 10C) is that the panelist should be supplied with the minimum flow required for breathing and that he or she should not inhale air from outside the sniffing port. Airflow rates of between 16 and 64 1/min (i.e. 0.96 to 3.84 m³/h) should be used depending upon the design of the sniffing port. The airflow rate passing through each sniffing port should be 16 1/min and the shape of each sniffing port was conical with a diameter of 7 cm and an angle of approximately 7 degrees.

Figure 3:
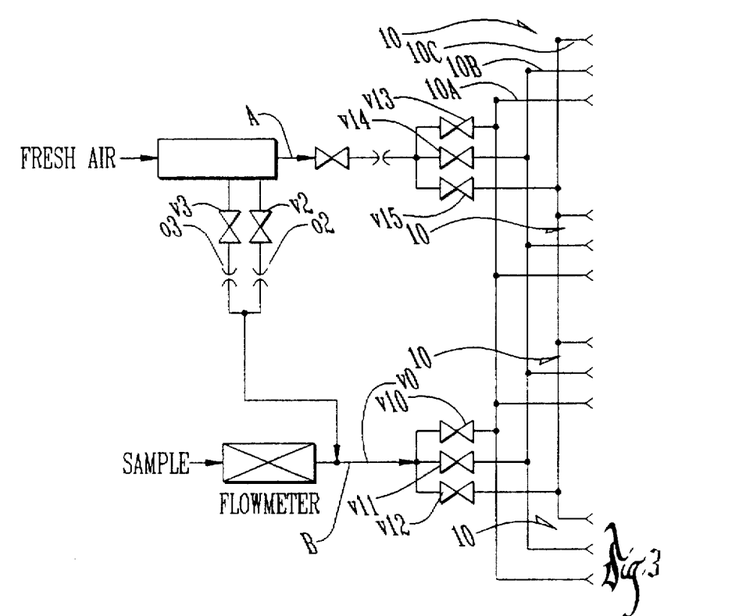
FIG. 3 is a schematic diagram of the distribution system.

FIG. 3 is a schematic diagram of the distribution system. The airflow rate of the air stream passing through each sniffing port is 16 1/min. The distribution system allows 4 panelists to work simultaneously and each panelist has access to three sniffing ports. There are twelve sniffing ports with a total airflow rate required of (12 Port)(16 1/min/port)=192 1/min The total airflow was derived from two air streams; the odor free air stream and the odorous air stream. The odor free air stream passes through line A, and is distributed to a total of 8 sniffing ports with valves $V_{13}$, $V_{14}$ and $V_{15}$. The maximum airflow rate for the odor-free air stream has a flow rate of:

(8 ports)(16 1/min/port)=128 1/min

The odor stream passes through line B as shown in FIG. 3 using one of the valves $V_{10}$, $V_{11}$ or $V_{12}$. The odorous stream is then distributed to four sniffing ports; one for each panelist. The odorous air stream has a flow rate of:

(4 ports)(16 1/min/port)=64 1/min

Figure 4:
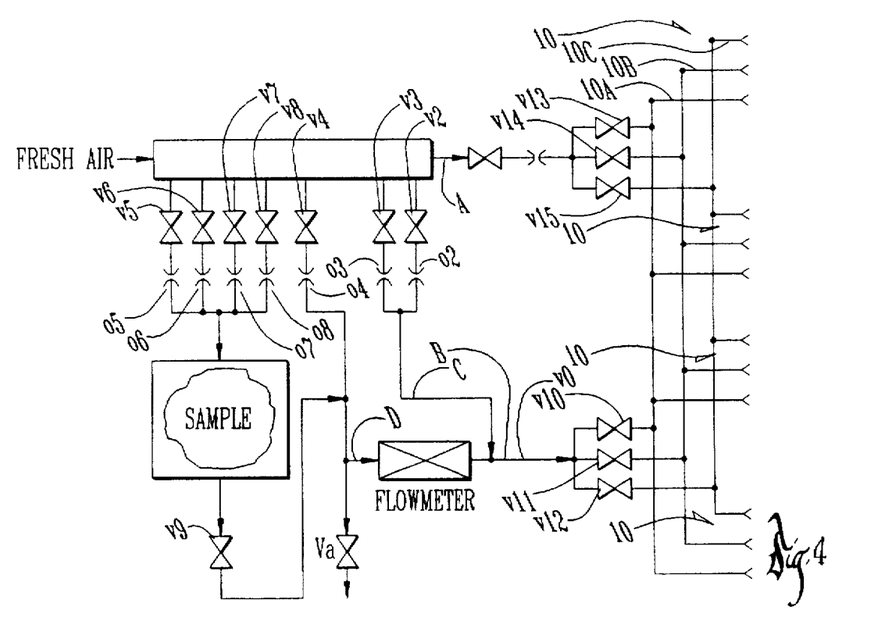
FIG. 4 is a view similar to that of FIG. 1 but shows the predilution mode.

The maximum dilution ratio (sample volume/total volume) required was selected as 1:16384 (1:$2^{14}$) with a step factor of 2, resulting in dilution ratios of: 1:$2^3$, 1:$2^4$, 1:$2^5$, ... 1:$2^{14}$ ($V_S$:$V_T$) where $V_S$ is the sample volume and $V_T$ is the total volume after dilution. The case of dilution ratio 1:$2^3$ without pre-dilution is shown in FIG. 4.

The diluted airflow rate passing through line B is 64 1/min and consists of two sources; one is the odor free airflow rate of 56 1/min passing through $V_2$ (and orifice $O_2$) ;the other one is the odorous air with a sample flow rate of 8 1/min which passes through valve $V_9$ (and orifice $O_9$) resulting in a dilution ratio of:

8/64=1:$2^3$

The case of dilution ratio 1:$2^8$ with pre-dilution will now be discussed. The electronic proportioning control valve (Va) can be continuously adjusted allowing the pre-diluted odorous air stream to pass through the flow meter at a flow rate QD of 4.7 1/min. The odor free air stream comes from valve $V_3$ (and orifice $O_3$) with an airflow $Q_{D1}$ of 62 1/min resulting in a total airflow rate through line D of:

4.7 1/min+62 1/min=66.7 1/min

The airflow rate satisfies the required dilution ratio of 1:256 and the odorous airflow rate through line D becomes:

$$Q_s = \frac{V_s}{V_T}(Q_D + Q_{D1}) = \frac{1}{256}(4.7 + 62) = 0.26 \text{ l/min}$$

The airflow rate of the stream passing through $V_3$ was defined as $Q_K$. The relationship between $Q_K$, $Q_S$, $Q_D$ and $Q_f$ is represented by Eqn. (1).

$$\frac{Q_S}{Q_D} = \frac{Q_K}{Q_K + Q_f}$$

where $Q_f$ is the pre-diluted odor free airflow rate of the stream which passes through valve $V_4$ (and orifice $O_4$) represented as:

$$Q_K = \frac{Q_S Q_f}{(Q_D - Q_S)}$$
$$= \frac{0.26 \times 62}{4.7 - 0.26}$$
$$= 3.6 \text{ l/min}$$

wherein:

$O_3$: Orifice for sample.

$Q_S$: Sample flow rate.

$Q_{pa, O4}$: Predilution airflow rate measured by orifice $O_4$.

$Q_{pa,f}$: Predilution flow rate measured by flow meter.

$O_d$: Orifice for diluted air.

$Q_d$: Diluted airflow rate measured by orifices $O_2$ and $O_3$. The DAAC (Data Acquisition, Data Analysis and Automatic Control System) of this invention provides panelists with a simple method for indicating which port they believe contains the odor. It also allows the olfactometer to signal to each panelist the start and finish of a test. The DAAC system developed for the olfactometer has the following components (see FIG. 5):

Four response buttons per panelist from which each panelist indicates the port believed to contain the odor;

A signal light which tells each panelist to begin sniffing and to indicate the conclusion of each test;

Data latches for each button that serve to store each panelist's response;

A multiplexing system that allows the data latches for each panelist to be read in sequence through a computer link;

A program used to analyze and process the data;

An input/output analog signal board for the input analog signal from the pressure transducer and flow meter and for sending out analog signals to each instrument;

A digital output signal board with relays for controlling the automatic valves;

A personal computer linked to the DAAC system.

Data Acquisition System

Figure 6:
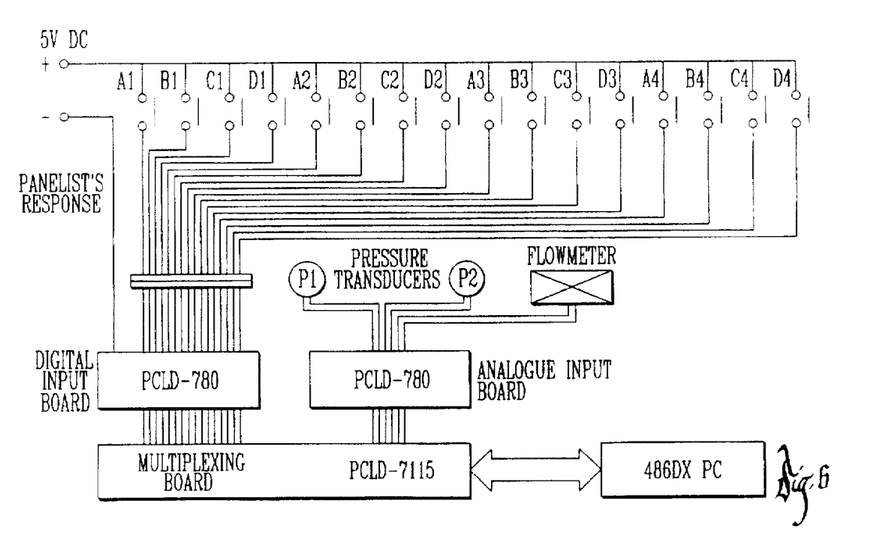
FIG. 6 is a schematic sketch of the data acquisition system.

The test starts at any one of the 12 possible dilution ratios ranging between 1:$2^3$ and 1:$2^{14}$. The panelists depress the corresponding button when he or she determines the sniffing port believed to contain the odorous sample. Each of the four panelists can change their choice at any time before they push the "accept" button D. The new data will replace the data which was already latched by the register. After all four panelists have "accepted" their choice, the data is transferred to the computer through a digital signal input board. If all the panelists do not detect the odor, the DAAC system automatically decreases the dilution ratio by one step and the panelists are instructed to continue. FIG. 6 is a schematic diagram of the data acquisition system.

Data Analysis System

FIG. 6 identified the schematic of the data analysis system. The hardware interface stores each panelists response in buffers. The digital input signal produced by each button (0 or 1) is transferred to binary code by the hardware interface. Buttons A1, B1, C1, D1, A2, B2, C2, and D2 used by the first and second panelist correspond to $2^0$, $2^1$, $2^2$, $2^3$, $2^4$, $2^5$, $2^6$, and $2^7$, respectively and in binary code range from;

0 0 0 0 0 0 0 0 to 1 1 1 1 1 1 1 1 and are stored in the 8-bit buffer 1. The same data format corresponding to buttons A3, B3, C3, D3, A4, B4, C4, and D4 for the third and fourth panelists were stored in the 8-bit buffer 2. The data analysis system processes the panelist's responses using the data sequence present in buffers 1 and 2.

When panelists activate a button by physically depressing it, logic sequences are stored in buffers 1 and 2. For example, assume that for a particular sample tested, panelists 1, 2, 3, and 4 perceived the odor present in sniffing ports A, B, C, and C, respectively. The binary code storing this data in buffers 1 and 2 is shown in Table 3. As shown in Table 3, the binary code from each panelist's response, stored in buffers 1 and 2, was identified as storage values $AA_1$, $AA_2$, $AA_3$, and $AA_4$, for panelists 1, 2, 3, and 4, respectively.

TABLE 3

Relation of the panelists and data

| panelist | button | buffer | storage | binary code |
|---|---|---|---|---|
| first | $A_1$ | 1 | $AA_1$ | 00000001 |
| second | $B_2$ | 1 | $AA_2$ | 00100000 |
| third | $C_3$ | 2 | $AA_3$ | 00000100 |
| fourth | $C_4$ | 2 | $AA_4$ | 01000000 |

A method was developed to detect when all panelists recorded the same response, resulting in two new storage values B and C. Values in B were the result of ANDing the values in buffers 1 and 2 with the 8-bit binary value 15, (00001111 or a hexadecimal H0F) where the ANDing operation was conducted bit-by-bit. The results are shown in Table 4 for the example response shown in Table 3. Values stored in C were the result of ANDing the values in buffers 1 and 2 with the 8-bit binary value 240 (11110000, or hexadecimal HF0), where again the ANDing operation was conducted bit-by-bit. The results are also shown in Table 4.

TABLE 4

The result of actual data AND reference data

| original A | binary code | B storage | A AND H0F | C storage | A AND HF0 |
|---|---|---|---|---|---|
| $AA_1$ | 00000001 | $BB_1$ | 00000001 | $CC_1$ | 00000000 |
| $AA_2$ | 00100000 | $BB_2$ | 00000000 | $CC_2$ | 00100000 |
| $AA_3$ | 00000100 | $BB_3$ | 00000100 | $CC_3$ | 00000000 |
| $AA_4$ | 01000000 | $BB_4$ | 00000000 | $CC_4$ | 01000000 |

The data values stored in C storage (Table 4) was shifted to the right 4 places by dividing the C storage by 16 as shown in Table 5. This shifted data is again ANDed with binary 15, bit-by-bit, to form a new storage value D, designated $DD_1$, $DD_2$, $DD_3$, and $DD_4$, for panelists 1, 2, 3, and 4, respectively (Table 5). Any change from the panelists were saved as new data in storage E replacing the original data from Storage A (See Table 6).

TABLE 5

Data shifting

| Data C | Binary code | Data C/16 | Data C/16 AND H0F | Storage D |
|---|---|---|---|---|
| $CC_1$ | 00000000 | xxxx0000 | 00000000 | $DD_1$ |
| $CC_2$ | 00100000 | xxxx0010 | 00000010 | $DD_2$ |
| $CC_3$ | 00000000 | xxxx0000 | 00000000 | $DD_3$ |
| $CC_4$ | 01000000 | xxxx0100 | 00000100 | $DD_4$ |

Table 6: The relationship of data B, data D and data E

TABLE 6

The relationship of data B, data D and data E

| Data B | Binary code | Data D | Binary code | E storage | Binary code |
|---|---|---|---|---|---|
| $BB_1$ | 0000 0001 | $DD_1$ | 0000 0000 | $EE_1$ | 0000 0001 |
| $BB_2$ | 0000 0000 | $DD_2$ | 0000 0010 | $EE_2$ | 0000 0010 |
| $BB_3$ | 0000 0100 | $DD_3$ | 0000 0000 | $EE_3$ | 0000 0100 |
| $BB_4$ | 0000 0000 | $DD_4$ | 0000 0100 | $EE_4$ | 0000 0100 |

The analysis system compares the data in storages B and D with the reference data H08, i.e. 0 0 0 0 1 0 0 0. If the data in storages B and D are smaller than H08, then the data in storages B and D which were not equal to zero were transferred to storage E. Table 6 shows the results of the example after performing this operation. Note that storage E contains the binary equivalent of the panelists original response. Recall that the sample presented, shown in Table 3, had panelists 1, 2, 3, and 4 selecting buttons A, B, C, and D, respectively which corresponds to binary code 00000001, 00000010, 00000100, and 00000100, respectively.

After the panelists push the "accept" button (D1, D2, D3 or D4), the storage G is created storing this information as shown in Table 7. After all four panelists have pushed the accept button D, the data in storage E is transferred to storage F. Storage F, as shown in Table 7, is the final accepted data from the four panelists, for the current dilution level.

TABLE 7

Final data

| Data G | Binary code | Data F | Binary code |
|---|---|---|---|
| $GG_1$ | 0000 1000 | $FF_1$ | 0000 0001 |
| $GG_2$ | 1000 0000 | $FF_2$ | 0000 0010 |
| $GG_3$ | 0000 1000 | $FF_3$ | 0000 0100 |
| $GG_4$ | 1000 0000 | $FF_4$ | 0000 0100 |

The above process in independent. If the first and second panelists push the "accept" button, only data $FF_1$ and $FF_2$ can transfer from Storage E to Storage F. The program will keep running until the responses from all four panelists are received.

After all the data is transferred to storage F, the data analysis system will check whether data $FF_1$, $FF_2$, $FF_3$, and $FF_4$ are all the same. If they are not the same, implying that all four panelists have not detected the odor, then the program will repeat the entire process with a new dilution level and will continue until all the data in storage F is equal. The analysis system will compare storage F with a randomly generated integer K which determines the sniffing port containing the odor. If data F is equal to integer K, the test is completed; otherwise, the dilution level will be decreased to a higher level and the program will repeat the entire process.

Automatic Control System (Feedback Control)

The feedback loop is the dominant technique used in process control. A representation of a feedback loop is given in FIGS. 7A and 7B in conjunction with the olfactometer and shows its applications to airflow rate control of a dilution system. The value of the controlled variable is measured with a flowmeter, and is compared with the desired value (also know as set point). The difference between the set point and the control variable is known as the controller error. The output of the controller is determined as a function of this error, and is used to adjust the manipulated variable.

In this dilution system, the flowmeter (OMEGA Engineering, Inc. Model FMMA-219) has its output change to a dc voltage varying between 0 v and 5 v corresponding to airflow rates between 0 l/min and 10 l/min. The received signal is then converted to a mathematical number, with 5 v corresponding to binary 4095 (12-bit A/D converter) while 0v corresponds to binary 0. There were 12 set points used for this dilution system corresponding to the 12 different dilution ratios. The program compares the input signals with the set points and measures the difference, or error.

Figure 7A:
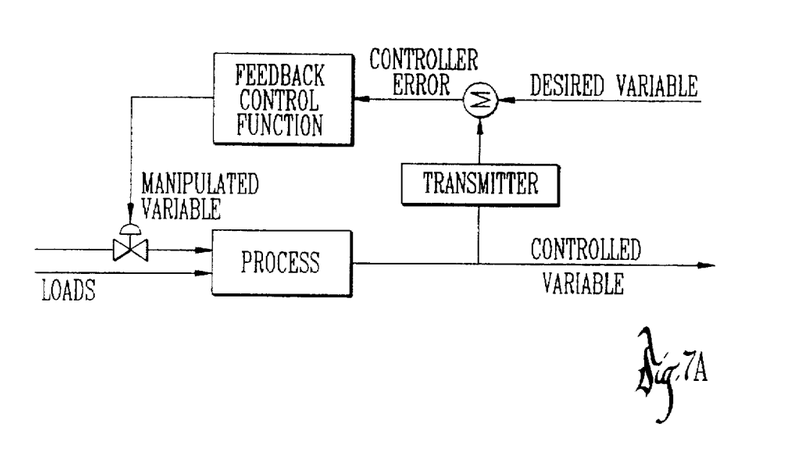
FIGS. 7A and 7B are schematic sketches of the feedback control system.
Figure 7B:
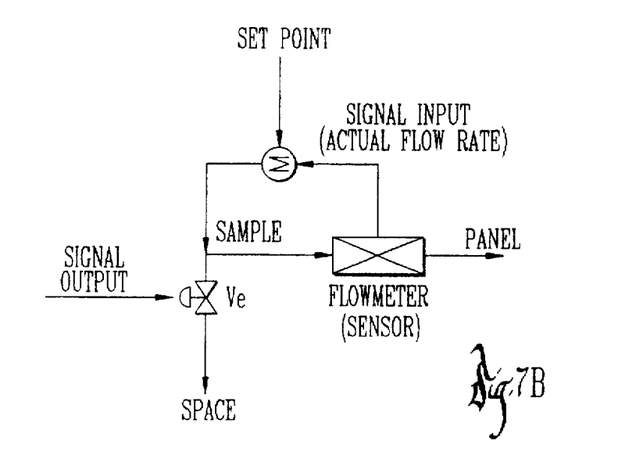

In the dilution system example as shown in FIGS. 7A and 7B, the set point was chosen as 2.3 l/min to satisfy a dilution ratio of 1:$2^9$. The set point 2.3 l/min was converted to binary 942 (2.3*4096/10) and stored in the computer. If the actual value measured by the flowmeter was 2.5 l/min, the analog output signal should be 1.25 v because 10 l/min corresponds to 5 v and the output of the flowmeter is linear. This signal was converted to binary 1024, and was compared with the set point 924 for an error of 82. The output signal was determined by a function of the error and the gain of the control. The relationship between the input and output signal at this point is the control action. If the gain was chosen as 40 then the output signal 3280 was converted to a 4 vdc voltage and was transmitted to the electronic proportioning control valve Va (FIG. 4), to adjust the flow rate of the stream which passes through the flowmeter. The feedback control loop was finally closed when the adjustment to the control valve Va affects the process, giving a new value of the measured variable received by the flowmeter.

The olfactometer of this invention is operated with the following steps:

Step 1. Operator secures an odorous sample and starts the olfactometer control system. The start-up control panel appears on the monitor.

Step 2. The operator activates the START button and is instructed to enter the sample name.

Step 3. After the sample name is entered, the operator is instructed to select the starting dilution level.

Step 4. The operator selects a number from 1 to 12 corresponding to the desired dilution level from $1.2^3$ to $1:2^{14}$, respectively. The control system begins establishing the desired dilution level and responds with "System increasing pressure, please wait". The pressure signal display in the "Sample Pressure Box" changes dynamically until the pressure reaches 2 PSI; the program responds with "Dilution is level A please begin sniffing".

Step 5. The four panelists begin sniffing their respective 3 ports and depress the button corresponding to the sniffing port which they perceive contains the odor. The response of the four panelists is displayed in the monitor by changing signal lights on the computer screen. There were 8 signal lights (4 for the evaluation buttons and 4 for the accept buttons) located on the monitor.

Step 6. If all four panelists select the correct port corresponding to the odorous sample twice, then the statement "Evaluation Successful" appears and the test concludes.

If the four panelists do not select the odorous sample, then the statement "Evaluation Failed, Increasing Dilution Level. Please Wait" appears and the control system adjusts the dilution to a new level and steps 5 and 6 are repeated.

If at the conclusion of the final dilution level ($1:2^3$) the four panelists still have not selected the odorous sample correctly, then the statement "Sorry, Sample is Odor Free" appears on the monitor and the test is concluded.

The olfactometer of this invention was developed for the measurement of odor concentration which will reduce test time, increase the range and accuracy of the dilution level, as well as provide for data acquisition and data analysis. Thus, the objects of this invention have been met.

What is claimed is:

1. An automated forced-choice dynamic-dilution olfactometer, comprising, an odor evaluation module comprising two or more panelist stations, a plurality of sniffing ports at each station, at least one signal element at each station operatively connected to a data control means, a plurality of separate air lines, each air line being simutaneously connected to each of the sniffing ports at each station so that individual panelists at each station can a plurality of separately sniff the air in each line, means for introducing an odor into one of said air lines so that each panelist can advise said data control means through said signal elements as to which air line is deemed to contain said odor and means operatively associated with the air line containing said odor to change the concentration of said odor after each of said panelists have signaled said data control means as to which air line contains said odor.

2. The device of claim 1 wherein each station has at least one signal element for each of said air lines.

3. The device of claim 2 wherein each station has an accept signal element to inform the data control means that the signals previously sent by any of said signal elements are final.

4. The device of claim 1 wherein said data control means includes a display screen to visibly show the response of said panelists as to which line contains an odor.

5. The device of claim 1 wherein said data control means includes a control element to automatically increase the odor concentration in the air line containing said odor if the panelists fail to correctly select the air line containing said odor so that said panelists can sample said sniffing ports again to detect the line containing said odor.

6. The method of detecting an odorous stream of air in an automated forced-choice dynamic-dilution olfactometer system, comprising, providing an odor evaluation module having two or more panelist stations, providing a plurality of sniffing ports at each station, providing at least one signal element at each station, and connecting the same to a data control means, providing a plurality of separate air lines, each air line being simultaneously connected to each of said sniffing ports at each station so that individual panelists at each station can separately sniff the air in each line, introducing an odor into one of said air lines, having the panelists at each station sniff each sniffing port to determine which air line contains said odor, having each panelist actuate said signal element to advise said data control system as to which air line contains said odor, and sequentially changing the concentration of odor of said air line containing said odor within the range of $1:2^3$ to $1:2^{14}$ in repetitive sequences of the aforesaid steps.

7. The method of claim 6 wherein the concentration of odor in said air line containing said odor is changed after each of said panelists have signaled said data control means as to which air line contains said odor, and then repeating the aforesaid steps.

8. The method of claim 6 wherein a separate signal element is provided for each sniffing port.

9. An automated forced-choice dynamic-dilution olfactometer, comprising, an odor evaluation module comprising two or more panelist stations, a plurality of sniffing ports at each station, at least one signal element at each station operatively connected to a data control means, separate air lines connected to one each of the sniffing ports at each station so that individual panelists at each station can separately sniff the air in each line, means for introducing an odor into one of said air lines so that each panelist can advise said data control means through said signal elements as to which air line is deemed to contain said odor, each station having at least one signal element for each of said air lines, and each station has an accept signal element to inform the data control means that the signals previously sent by any of said signal elements are final.

10. The method of detecting an odorous stream of air in an automated forced-choice dynamic-dilution olfactometer system, comprising, providing an odor evaluation module having two or more panelist stations, providing a plurality of sniffing ports at each station, providing at least one signal element at each station, and connecting the same to a data control means, providing separate air lines to one each of said sniffing ports at each station so that individual panelists at each station can separately sniff the air in each line, introducing an odor into one of said air lines, having the panelists at each station sniff each sniffing port to determine which air line contains said odor, having each panelist actuate said signal element to advise said data control system as to which air line contains said odor, and repeating the foregoing steps with an increased level of odor being introduced into said one of said air lines if said panelists have not all correctly advised said data control system as to which air line contains said odor.

11. The method of claim 10 wherein the foregoing steps are repeated in separate sequences and the level of odor is sequentially increased after each repetitive sequence until said panelists have all correctly advised said data control system as to which air line contains said odor.

12. The method of claim 11 wherein the level of odor introduced into said one air line is within the range of $1.2^3$ to $1.12^{14}$ in repetitive sequences of the aforesaid steps.

13. The method of claim 10 wherein the level of odor introduced into said one air line is within the range of $1.2^3$ to $1.12^{14}$ in repetitive sequences of the aforesaid steps.

* * * * *

UNITED STATES PATENT AND TRADEMARK OFFICE
CERTIFICATE OF CORRECTION

PATENT NO. : 5,767,385
DATED : June 16, 1998
INVENTOR(S) : Dwaine S. Bundy; Wen-Hua Huang; Steven J. Huff; Qianbao Liu; and Xiwei Li It is certified that error appears in the above-identified patent and that said Letters Patent is hereby corrected as shown below:

Column 9, line 53, should be corrected to read as follows:

- can separately sniff the air in each line, -

Column 11, lines 1, 2 and 3 should be corrected to read as follows:

- providing a plurality of separate air lines, each air line being simultaneously connected to each of said sniffing ports at each station so that individual panelists at each station can separately sniff the air in each line, -

Signed and Sealed this

Twenty-seventh Day of October, 1998

BRUCE LEHMAN

Attest:

Attesting Officer    Commissioner of Patents and Trademarks